United States Patent [19]

Wilton et al.

[11] Patent Number: 4,661,353

[45] Date of Patent: * Apr. 28, 1987

[54] CL-1577-B$_4$ COMPOUND, ITS PRODUCTION AND USE

[75] Inventors: John H. Wilton; Gerard C. Hokanson; James C. French, all of Ann Arbor, Mich.

[73] Assignee: Warner-Lambert Company, Morris Plains, N.J.

[*] Notice: The portion of the term of this patent subsequent to Jul. 23, 2002 has been disclaimed.

[21] Appl. No.: 804,411

[22] Filed: Dec. 4, 1985

Related U.S. Application Data

[62] Division of Ser. No. 712,294, Mar. 15, 1985, Pat. No. 4,594,248.

[51] Int. Cl.$^4$ .................... A61K 35/74; C12P 1/06
[52] U.S. Cl. ............................ 424/123; 424/117; 435/169
[58] Field of Search ............... 424/117, 123; 435/169

[56] References Cited

U.S. PATENT DOCUMENTS 4,530,835 7/1985 Bunge et al. ................. 424/117

Primary Examiner—Jerome D. Goldberg
Attorney, Agent, or Firm—Jerry F. Janssen

[57] ABSTRACT

CL-1577-B$_4$ compound is derived by the solvolysis under anhydrous conditions of either CL-1577A compound of CL-1577B compound; obtained from the fermentative action of a purified strain of Actinomycete designated ATCC 39363 under aerobic conditions.

CL-1577-B$_4$ compound is a potent antimicrobial agent, possessing activity against a number of gram-positive and gram-negative bacteria, yeasts, and fungi. In addition, the compound exhibits in vivo activity against the P388 murine leukemia cell line and in vitro activity against the L1210 murine leukemia cell line.

A method of making the compound as well as pharmaceutical compositions and methods for their use are also disclosed.

1 Claim, 4 Drawing Figures

CL-1577-B₄ COMPOUND, ITS PRODUCTION AND USE

CROSS-REFERENCE TO RELATED APPLICATIONS

This application is a divisional of U.S. application Ser. No. 712,294 filed Mar. 15, 1985, now U.S. Pat. No. 4,594,248.

BACKGROUND OF THE INVENTION

The present invention relates to antibiotic substances and methods for their production and use. More particularly, it is concerned with the antibiotic substance CL-1577-B₄, pharmaceutical compositions containing the compound, and methods for its production and use.

SUMMARY OF THE INVENTION

In accordance with one aspect of the present invention, there is provided tne antibiotic substance CL-1577-B₄ which exhibits activity against a number of gram-positive and gram-negative bacteria as well as certain yeasts and filamentous fungi. Additionally, the compound demonstrates in vitro activity against the L1210 and in vivo activity against the P388 murine leukemia cell lines.

In accordance with another aspect of the present invention, there is provided a metnod of preparing CL-1577-B₄ comprising the steps of first cultivating a purified isolate of the microorganism designated ATCC 39363 under aerobic conditions in a nutrient broth containing assimilable sources of carbon and nitrogen until a sufficient quantity of the compounds CL-1577A or CL-1577B are produced, then isolating the CL-1577A or CL-1577B from the nutrient broth, and subsequently converting the CL-1577A or CL-1577B compound to CL-1577-B₄ compound by solvolysis.

In accordance with a further aspect of the present invention, there are provided pharmaceutical compositions useful in the treatment of microbial infections in a mammal comprising an antimicrobially effective amount of compound CL-1577-B₄ in combination witn a pharmaceutically acceptable carrier.

In accordance with another aspect of the present invention, there is provided a method of treating microbial infections in a mammal comprising administering to a mammal in need of such treatment a pharmaceutical composition comprising an antimicrobially effective amount of compound CL-1577-B₄ in combination with a pharmaceutically acceptable carrier.

In accordance with yet another aspect of the present invention, there are provided pharmaceutical compositions comprising a cytotoxically effective amount of compound CL-1577-B₄ in combination with a pharmaceutically acceptable carrier.

In accordance with another aspect of the present invention, there is provided a method of treating tumors in a mammal comprising the administration to a mammal in need of such treatment a pharmaceutical composition comprising a cytotoxically effective amount of CL-1577-B₄ compound in combination with a pharmaceutically acceptable carrier.

DETAILED DESCRIPTION

Figure 1:
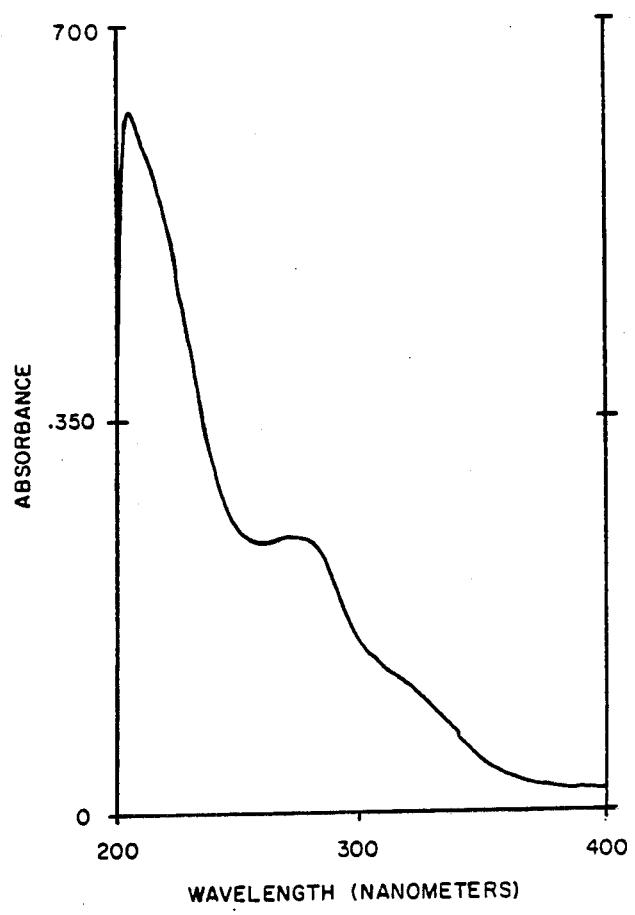
FIG. 1 represents the ultraviolet spectrum of CL-1577-B₄ compound in methanolic solution.

In accordance with the present invention, CL-1577-B₄ antibiotic compound is prepared by first cultivating a selected isolate of Actinomycete, designated ATCC 39363, under artificial conditions of aerobic fermentation to produce sufficient quantities of the compounds CL-1577A and/or CL-1577B to permit their isolation from the nutrient broth by conventional means. The CL-1577A and/or CL-1577B compounds are isolated from the nutrient broth and subsequently converted to the compound CL-1577-B₄, which is a molecular fragment common to both CL-1577A and CL-1577B, by chemical solvolysis reaction.

Although differing in molecular structure, compounds CL-1577A and CL-1577B possess the same substructural unit, CL-1577-B₄, which can be obtained from either of the parent compounds by acidolysis, preferably in an anhydrous acidic medium such as, for example, anhydrous methanolic HCl.

As further set out below, CL-1577-B₄ compound possesses activity against a number of microorganisms as well as demonstrating activity against the L1210 murine leukemia cell line in vitro and against transplanted P388 murine leukemia cell line in vivo.

The actinomycete isolate suitable for the purposes of preparing the CL-1577A and CL-1577B intermediate compounds of this invention was found in a soil sample collected in Tennessee, USA. This microorganism was isolated from the soil sample using a suitable agar plating medium containing salts such as potassium chloride, magnesium sulfate, and ferrous sulfate, and carbon sources such as glycerol and asparagine.

To isolate the microorganism, the soil sample was pretreated with calcium carbonate before being plated onto the agar medium and, once plated, was incubated at a favorable temperature, particularly 33° C., to allow for the development of the soil microoganisms.

The organism producing the CL-1577 complex was isolated from the soil sample by the agar plating technique and is an as yet unidentified Actinomycete which has been deposited with the American Type Culture Collection, Rockville, Md., USA, 20852, where it is being maintained in their permanent culture collection as ATCC Deposit 39363. This microorganism, which produces CL-1577A and CL-1577B, is also being maintained as a dormant culture in lyophile tubes, cryogenic vials, and in soil tubes in the Warner-Lambert/Parke-Davis Culture Collection, 2800 Plymouth Rd., Ann Arbor, Mich., USA, 48105, where it bears the designation WP-444.

The compounds CL-1577A and CL-1577B are produced by isolate ATCC 39363 during aerobic fermentation under controlled artificial conditions. The fermentation medium consists of sources of carbon, nitrogen, minerals, and growth factors. Examples of suitable carbon sources are glycerol and various simple sugars such as glucose, mannose, fructose, xylose, ribose, or other carbohydrate-containing compounds such as dextrin, starch, corn meal, and whey. The normal quantity of carbon source materials in the fermentation medium varies from about 0.1 to about 10 weight percent.

Nitrogen sources in the fermentation medium are organic, inorganic, or mixed organic-inorganic materials. Examples of such materials are cottonseed meal, soybean meal, corn germ flour, corn steep liquor, distillers dried solubles, peanut meal, peptonized milk, and various ammonium salts.

The addition of minerals and growth factors to the medium are also helpful in the production of the CL-1577A and CL-1577B compounds. Examples of fermentation medium mineral additives include potassium chloride, sodium chloride, ferrous sulfate, calcium carbonate, cobaltous chloride, and zinc sulfate. Sources of growth factors include various yeast and milk products.

The preferred method for producing the CL-1577A and CL-1577B compounds is by submerged culture fermentation. According to this method, the fermentation broth ingredients are prepared in solution or suspension and the resulting mixture is sterilized by autoclaving or by steam heating. The pH of tne aqueous medium is adjusted to preferably between about pH 4 and about pH 8 and the mixture is cooled following sterilization to a temperature between about 16° C. to about 45° C. The cooled, sterile fermentation broth is inoculated with the microorganism and thereafter fermentation is carried out with aeration and agitation.

In the submerged culture method, fermentation is carried out in shake-flasks or in stationary tank fermentors. In shake-flasks, aeration is achieved by agitation of the flasks to bring about mixing of the medium with air. In stationary tank fermentors, agitation is provided by impellers which may take the form of disc turbines, vaned discs, open turbine or marine propellers. Aeration is accomplished by injecting air or oxygen into the agitated mixture.

Adequate production of the CL-1577A and CL-1577B compounds is normally achieved under these conditions after a period of two to ten days.

In an alternative method, the CL-1577A and CL-1577B compounds may also be prepared by solid state fermentation of the microorganism whereby the microorganism is grown on the surface of an appropriate solid culture medium.

The following examples of fermentative methods of preparing CL-1577A and CL-1577B are provided to enable one skilled in the art to practice the present invention. They are not to be viewed as limiting the scope of the invention as it is defined by the appended claims.

Fermentative Production of CL-1577A and CL-1577B Compounds

EXAMPLE 1

The purified isolate of microorganism, designated ATCC 39363, following its isolation from the soil sample on a suitable a9ar plating medium, was transferred to an agar slant tube containing CIM 23 nutrient medium, and incubated at 28° C. for seven to fourteen days.

TABLE 1

| Formulation of CIM 23 Nutrient Medium | |
|---|---|
| Amidex corn starch | 1.0% |
| N-Z Amine, Type A | 0.2% |
| Beef Extract (Difco) | 0.1% |
| Yeast Extract (Difco) | 0.1% |
| Cobalt Chloride Pentahydrate | 0.002% |
| Agar | 2.0% |

TABLE 1-continued

| Formulation of CIM 23 Nutrient Medium | |
|---|---|
| Water (to make) | 100.0% |

EXAMPLE 2

A portion of the microbial growth from the agar slant tube was used to inoculate the 18-mm×150 mm tube containing 5 ml of ARM 1550 seed medium. The inoculated seed medium was shaken at 33° C. for three days.

TABLE 2

| Formulation of ARM 1550 Nutrient Medium | |
|---|---|
| Bacto-Yeast Extract (Difco) | 0.5% |
| Glucose Monohydrate | 0.1% |
| Soluble Starch (Difco) | 2.4% |
| Bacto-Tryptone (Difco) | 0.5% |
| Bacto-Beef Extract (Difco) | 0.3% |
| Calcium Carbonate | 0.2% |
| Water (to make) | 100.0% |

Note:
The pH of the medium was adjusted to 7.5 with NaOH prior to adding the calcium carbonate

EXAMPLE 3

A 1-ml portion of the microbial growth from the seed tube was transferred to a 300-ml baffled shakeflask containing 50 ml of SM-13 production nutrient medium.

TABLE 3

| Formulation of SM-13 Nutrient Medium | |
|---|---|
| Dextrin-Amidex B411 (American Maize) | 1.5% |
| Lactose (Mallinkrodt) | 1.0% |
| Pharmamedia (Traders) | 0.65% |
| Fish Meal (Zapata Haynie) | 0.35% |
| Torula Yeast (St. Regis) | 0.25% |

The inoculated flask contents were incubated at 35° C. for four days with shaking (170 rpm gyratory shaker, 5 cm throw). After a five day period, the fermentation beer was tan in color, the mycelia was granular in appearance, and the pH of the beer was about 6.4.

EXAMPLE 4

A cryogenically preserved sample containing approximately 1 ml of a suspension of the ATCC 39363 isolate culture was used to inoculate 600 ml of SD-05 seed medium contained in a 2-liter baffled shake flask. The inoculated flask contents were incubated for 76 hours at 33° C. while being shaken on a gyratory shaker at 130 rpm (5 cm throw).

TABLE 4

| Formulation of SD-05 Nutrient Medium | |
|---|---|
| Amberex 1000 (Amber Laboratories) | 1.0% |
| Glucose monohydrate | 0.2% |
| Dextrin-Amdex B 411 (American Maize) | 0.1% |
| N-Z Case (Humko Sheffield) | 0.1% |
| Spray-Dried Meat Solubles (Daylin) | 0.002% |
| Agar | 2.0% |
| Water (to make) | 100.0% |

After 76 hours, the contents of the seed flask were transferred aseptically to a 30-liter stainless steel fermentor containing 16 liters of SD-05 seed medium. The inoculated fermentor contents were incubated at 33° C. for 24 hours while being stirred at 300 rpm and sparged with air at a rate of 1 vol/vol/min.

EXAMPLE 5

The microbial growth from Example 4 was used to inoculate 75 gallons (284 liters) of SD-05 seed medium contained in a 200-gallon (757-liter) stainless steel fermentor. The medium was sterilized by steam heating at 121° C. for 40 minutes after which the fermentor and contents were cooled to 33° C. and inoculated with about 16 liters of the microorganism-containing broth from Example 4. The resulting mixture was incubated at 33° C. for about 20 hours with stirring at 155 rpm while being sparged with air at a rate of about 0.75 vol/vol/min.

EXAMPLE 6

The microbial growth from Example 5 was used to inoculate about 1300 gallons (4921 liters) of SM-121 nutrient medium contained in a 2000-gallon (7571liter) stainless steel fermentor. The medium was sterilized prior to inoculation by heating with steam for 40 minutes at 121° C. After sterilization, the fermentor and contents were cooled to 33° C., inoculated, and incubated for five days with stirring at 125 rpm and air sparging at a rate of about 0.75 vol/vol/min.

The SM-121 medium consisted of 1.75% by weight of a feed grade mixture composed of soybean meal, ground yellow corn, ground wheat, corn gluten meal, wheat middlings, dried milk products, animal fat preserved with BHA, ground beet pulp, calcium carbonate, sucrose, dehydrated alfalfa meal, dicalcium phosphate, brewers dried yeast, salt, vitamin $B_{12}$ supplement, calcium pantothenate, niacin, choline chloride, menadione sodium bisulfate (source of vitamin K activity), folic acid, pyridoxin hydrochloride, thiamin, ascorbic acid, vitamin A supplement, D activated animal sterol (source of vitamin $D_3$), vitamin E supplement, iron carbonate, iron sulfate, calcium iodate, manganous oxide, copper oxide, cobalt carbonate, and zinc oxide.

The fermentation cycle was monitored by measuring and recording such fermentation parameters as pH and percent sedimentation. The data appear in Table 5.

TABLE 5

| Fermentation Time (Hours) | pH | Percent Sedimentation (Growth) |
|---|---|---|
| 0 | 6.65 | 0 |
| 24 | 8.10 | 10.0 |
| 46 | 7.40 | 29.3 |
| 75 | 7.30 | 25.4 |
| 96 | 7.90 | 20.0 |
| 116 | 8.20 | 25.4 |

After 116 hours of fermentation, the 1140 gallons (4315 liters) of fermentation beer were harvested and the CL-1577A and Cl-1577B compounds isolated as described below.

Chemical Isolation of CL-1577A and CL-1577B

EXAMPLE 7

Unfiltered fermentation beer (4500 liters) was stirred for two hours with 3200 liters EtOAc. The mixture was treated with 115 kg Celite 545 and then filtered through a plate and frame filter press. The filter cake was washed twice with 280 liter portions of EtOAc and the washes were added to the filtrate. The lower aqueous layer was separated and the organic extract was concentrated in vacuo to 29.5 liters. This concentrate was diluted with 91 liters petroleum ether and the mixture was extracted with 22 liters of MeOH-$H_2O$ (1:1). The lower aqueous methanol layer (25 liters) was extracted with seven liters petroleum ether and then concentrated to three liters. All of the organic-soluble material that remained was carefully transferred to nine liters EtOAc. This solution was dried ($Na_2SO_4$) and concentrated to two liters. The concentrate was diluted with four liters $CH_2Cl_2$ and stored overnight at $-20°$ C. Insoluble material was removed by filtration using 200 g Celite 545. After filtration the Celite pad was washed with one liter $CH_2Cl_2$ EtOAc (2:1). The washes and filtrate were combined (seven liters) and diluted with 1.5 liters $CH_2Cl_2$. This solution was added to a 10 cm (ID) column containing 8.2 kg of 40 μm aminopropyl-silica gel (Analytichem International, Inc., Harbor City, Calif.) packed in $CH_2Cl_2$. The resin was then eluted sequentially with 44 liters $CH_2Cl_2$; 80 liters of $CHCl_3$ containing 35–20% $CH_2Cl_2$; and finally with 30 liters of $CHCl_3$: EtOH (95:5). A head pressure of 0.70 kg/cm² was used to maintain a flow rate of approximately 400 ml/min. A total of 24 fractions were collected in volumes of 2–16 liters. HPLC analysis of each fraction showed that the majority of the CL-1577A was eluted with $CHCl_3$-$CH_2Cl_2$ (80:20) (Eluate A) and most of the CL-1577B was eluted with $CHCl_3$-EtOH (95:5) (Eluate B). Eluate A (61 liters) was concentrated in vacuo to 150 ml. The concentrate was treated with 1.2 liters petroleum ether to precipitate 3.04 g of solid (Product A). HPLC showed that Product A contained 1.29 g of CL-1577A and 0.396 g of CL-1577B. Eluate B (19.5 liters) was similarily processed to yield 4.15 g of a solid (Product B) that contained 0.47 g of CL-1577A and 1.75 g of CL-1577B.

Chemical Isolation of CL-1577A and CL-1577B Compounds

EXAMPLE 8

A 7 cm (ID)×88 cm stainless steel column was dry-packed with 1.9 kg of 40 μm $C_{18}$-silica gel (Analytichem). After the adsorbent was washed with ten liters of MeOH-0.05 M $NH_4OAc$ (pH 6.8) buffer (75:25), a solution of Product A (3.04 g) in 20 ml of MeOH-$H_2O$ (9:1) was applied to the top of the column. For chromatography, MeOH-0.05 M $NH_4OAc$ (pH 4.8) buffer (70:30) was used as the eluent at a head pressure of approximately 10.6 kg/cm². Each of the 20 fractions collected (total volume=39 liters) was analyzed by HPLC. The majority of the CL-1577A eluted between 7-18 liters; the smaller amount of CL-1577B present in Product A was subsequently eluted using 15.5 liters of MeOH-0.1 M NaOAc (pH 4.8) buffer (75:25). The fractions (11 liters) containing most of the CL-1577A were combined and concentrated in vacuo to remove MeOH. The aqueous mixture was extracted with $CHCl_3$. The organic extract was washed with $H_2O$, dried over $Na_2SO_4$ and concentrated to about 150 ml. Ten volumes of cyclohexane was added to precipitate 892 mg of a solid that contained about 500 mg of CL-1577A and <50 mg of CL-1577B. This product was further purified by reverse phase chromatography on $C_{18}$-silica gel using a Prep LC/System 500 instrument (Waters Associates, Milford, Mass.) fitted with a PrepPAK-500/$C_{18}$ column. The charge (0.88 g) was triturated with 9 ml MeOH. Insoluble material was removed by centrifugation. The supernatant solution was diluted with 1 ml $H_2O$ and added to the top of the column. Chromatography was effected using 17 liters of MeCN-MeOH-0.1M NaOAc (pH 4.4) buffer (38:8:54), adjusted to pH 4.8 with HOAc prior to use. The fractions eluting between 9-15 liters contained CL-1577A as the only UV-absorbing component. These were combined (seven liters) and concentrated at <30° C. to remove organic solvents. The concentrate was extracted three times with $CHCl_3$. The extracts were combined, extracted twice with one-third volumes of $H_2O$, and dried over $Na_2SO_4$. The $CHCl_3$ solution was concentrated to 25 ml (<25° C.) and then treated with 500 ml n-pentane to precipitate 273 mg of CL-1577A (>95% pure by HPLC).

A solution of Product B (4.0 g), described above, in 30 ml $MeOH-H_2O$ (9:1) was chromatographed over 1.9 kg of 40 μm $C_{18}$-silica gel contained in a 7 cm (ID) column. The eluent was 51 liters of MeOH-0.05 M $NH_4OAc$ (pH 6.8) buffer (75:25). Each of the 25 fractions collected was analyzed by HPLC. CL-1577A was eluted between 13.5–24 liters and CL-1577B was eluted between 31–50 liters. The latter eluate was concentrated in vacuo to one liter. The turbid concentrate was extracted three times with $CHCl_3$. The organic extracts were combined, washed twice with $H_2O$, and dried over anhydrous $Na_2SO_4$. The $CHCl_3$ solution was concentrated to 50 ml and then treated with 500 ml of cyclohexane to precipitate 930 mg of a pale yellow solid. HPLC showed that this product contained 760 mg of CL-1577B. This material was further purified, in three separate runs, using a Prep LC/System 500 instrument fitted with a PrepPAK-500/$C_{18}$ column. Each portion (310 mg) of the starting charge was dissolved in 5.4 ml MeOH. Insoluble material was removed by centrifugation. The supernatant solution was treated with 0.6 ml $H_2O$ and applied to the $C_{18}$-silica gel column. The mobile phase was prepared by adjusting a 67:33 mixture of MeOH-0.1 M NaOAc (pH 4.4) buffer to pH 4.8 with HOAc. Approximately nine liters of eluent was required for each of the three column runs which were completed and worked up within 12 hours. The course of each of the three chromatographic separations was monitored by HPLC. The majority of CL-1577B eluted between 5–8.5 liters. The fractions that contained CL-1577B as the only UV absorbing component were combined and quickly concentrated in vacuo to remove MeOH. The aqueous mixture was extracted twice with $CHCl_3$. The $CHCl_3$ extracts were combined, dried ($Na_2SO_4$), and concentrated to 45 ml. Cyclohexane (two liters) was added to precipitate 503 mg of CL-1577B which was >98% pure by HPLC analysis.

Preparation of CL-1577-$B_4$ Compound from CL-1577A Compound

EXAMPLE 9

CL-1577A compound (127 mg) was dissolved in 11 ml of methanol and 11 ml of anhydrous 1.0 M methanolic HCl was added over a period of one minute. The course of the solvolysis reaction was monitored by high pressure liquid chromatographic (HPLC) techniques using the system described below. Aliquots for analysis were prepared by diluting 5 μl of reaction mixture with 45 μl of 1.0 M ammonium acetate buffer (pH 8), and 5 μl of the resulting solution was used for the chromatographic analysis. After the reaction had come to completion (25 minutes at room temperature), the mixture was diluted with 180 ml of 0.05 M ammonium acetate (pH 6.5) and the pH was adjusted to 5.5 with 1 N ammonium hydroxide solution. The resulting solution was immediately applied to an mm (ID)×29 cm glass chromatographic column containing 16.6 g of 40 μm Sepralyte $C_{18}$ silica gel (Analytichem International, Inc., Harbor City, Calif.) which had been previously washed with 200-ml portions of methanol, 50% aqueous methanol, and methanol:acetonitrile:0.05 M ammonium acetate buffer (pH 6.5), (2.8:7.2:90). The column was eluted with a linear solvent gradient at a flow rate of 4 ml/min using an automatic gradient controller. The parameters of this elution appear in Table 6.

TABLE 6
Gradient Eluate for $C_{18}$ Silica Gel
Purification of CL-1577-$B_4$

| Time (min) | Percent Buffer* | Percent Organic** |
|---|---|---|
| 0 | 90 | 10 |
| 16 | 90 | 10 |
| 76 | 60 | 40 |
| 136 | 40 | 60 |
| 176 | 20 | 80 |
| 196 | 0 | 100 |
| 206 | 0 | 100 |

*Buffer - 0.05 M ammonium acetate (pH 6.5)
**Organic - methanol:acetonitrile (2:5)

Column eluates (collected as 8 ml fractions) were assayed by high pressure liquid chromatography (HPLC), antimicrobial disk assays, and cytotoxicity as measured against the L1210 murine leukemia cell line. Fractions 57–62 of the eluate were combined and diluted with one volume of 10% sodium chloride and the resulting solution extracted several times with chloroform. The combined chloroform extracts were washed once with water and the chloroform evaporated in vacuo at room temperature to yield 67.4 mg of CL-1577-$B_4$ compound as a pale yellow solid. The material was found to have a greater than 95% purity by HPLC analysis.

EXAMPLE 10

Preparation of CL-1577-$B_4$ Compound from CL-1577B Compound

CL-1577-$B_4$ compound is prepared from CL-1577B in the same manner as described above in Example 9. CL-1577B is solvolyzed in anhydrous methanolic HCl to yield CL-1577-$B_4$, which is then subsequently purified by chromatographic methods using $C_{18}$ silica gel as detailed in Example 9 above.

Properties of CL-1577-$B_4$ Compound

The physical and spectral properties of CL-1577-$B_4$ compound are given in Table 7 together with the appropriate reference (where applicable) to the Figure illustrating the spectrum.

TABLE 7
Physical and Spectral Properties
of CL-1577-$B_4$ Compound

Figure 2:
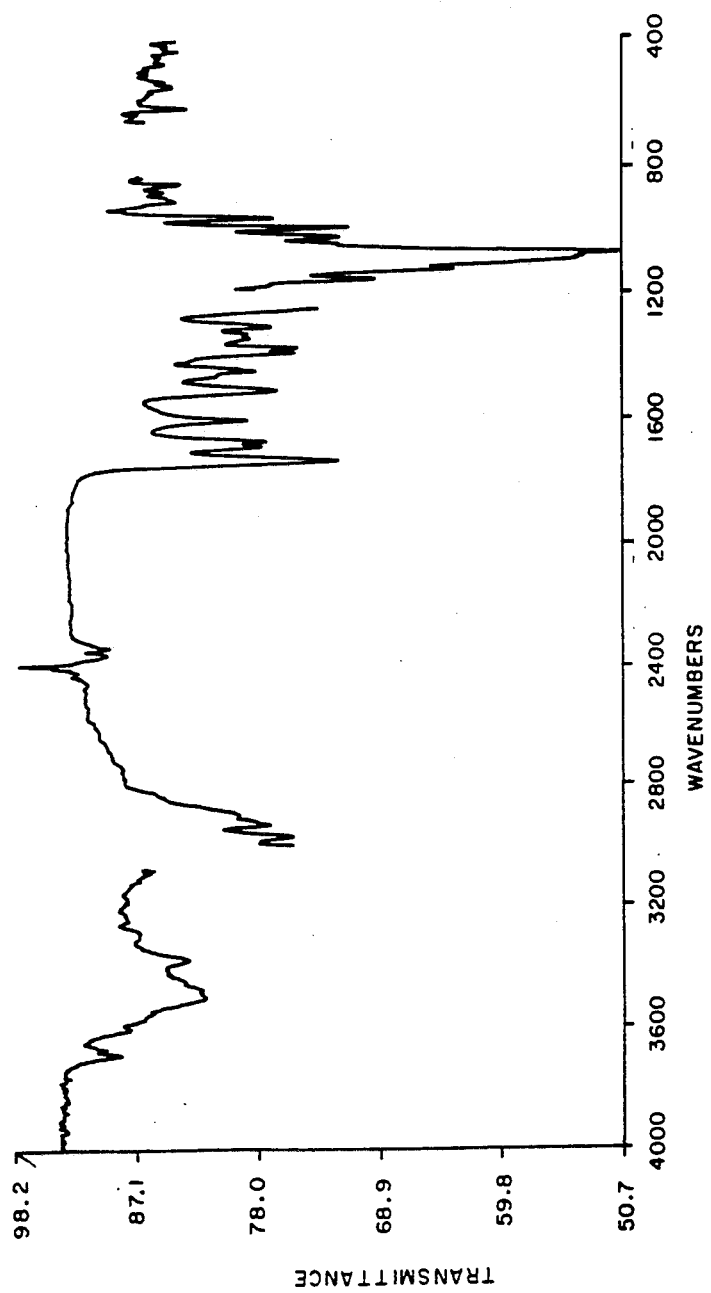
FIG. 2 represents the infrared spectrum of CL-1577-B₄ compound.
Figure 3:
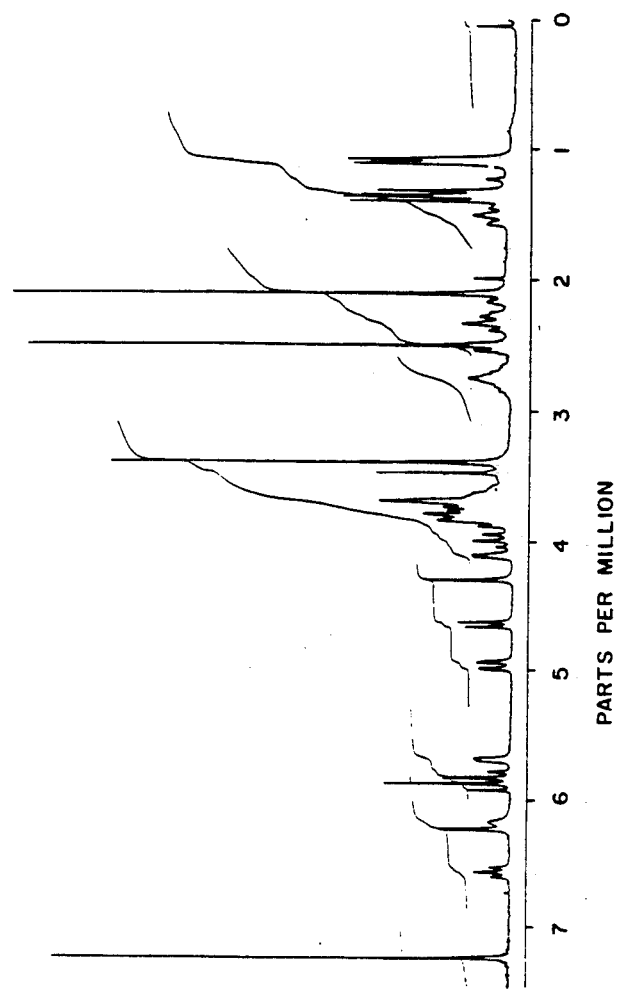
FIG. 3 represents the 200 MHz proton magnetic resonance spectrum of CL-1577-B₄ compound in deuteriochloroform solution.

| | |
|---|---|
| Physical State | Solid |
| Color | Pale Yellow |
| Apparent Molecular Weight | 855 atomic mass units (FAB mass spectrometry) |
| Elemental Analysis | 47.8% C; 5.74% H; 3.88% N; 30.66% O (by difference); 11.92% S |
| Ultraviolet absorption spectrum (FIG. 1) | 315 nm (inflection), 271 nm (a = 10.8), 213 nm (inflection) |
| Infrared absorption spectrum (FIG. 2) | Principal absorption peaks at 3700, 3500, 3180, 2975, 2930, 1735, 1682, 1670, 1603, 1508, 1500, 1383, 1369, 1302, 1154, 1100, 1075, 1020, 990, and 859 reciprocal centimeters |
| 200 MHz proton magnetic resonance spectrum in deuteriochloroform (FIG. 3) | Principal signals at 1.10 (doublet), 1.34 (doublet), 1.39 (doublet), 1.51 (broad double doublet), 2.10 (singlet), 2.13 (doublet of double doublets), |

TABLE 7-continued

Physical and Spectral Properties
of CL-1577-B4 Compound

Figure 4:
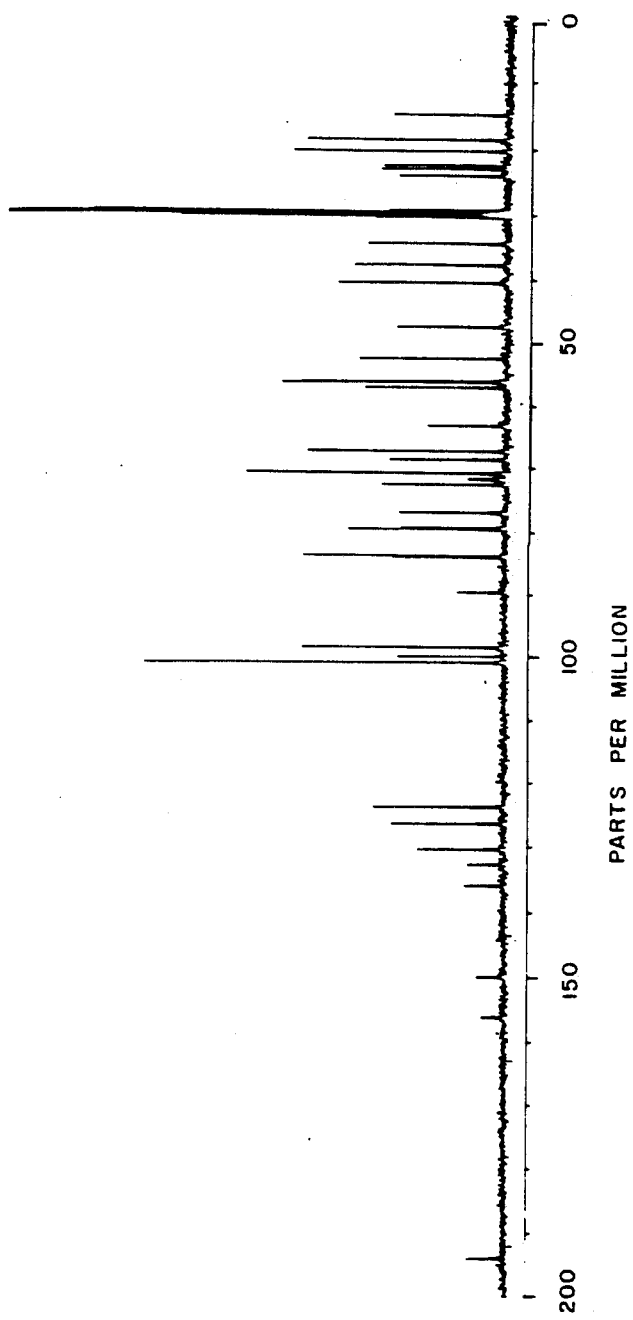
FIG. 4 represents the 90.56 MHz $^{13}$C magnetic resonance spectrum of CL-1577-B₄ compound in hexadeuteroacetone solution.

|  |  |
|---|---|
|  | 2.30 (multiplet), 2.49 (singlet), 2.50 (doublet of doublets), 2.76 (multiplet), 3.39 (singlet), 3.88-3.4 (multiplet), 3.99 (doublet of doublets), 4.11 (doublet of double doublets), 4.29 (singlet), 4.63 (doublet), 4.96 (doublet of doublets), 5.68 (broad doublet), 5.79 (doublet of doublets), 5.88 (doublet), 6.17 (multiplet), 6.22 (doublet), and 6.56 (doublet of doublets) parts per million downfield from tetramethylsilane |
| 90.56 MHz carbon magnetic resonance spectrum in hexa-deuterioacetone (FIG. 4) | Principal singals at 193.8, 156.0, 149.8, 136.0, 132.7, 130.3, 126.3, 123.6, 100.8, 99.8, 98.4, 89.5, 84.1, 83.8, 79.5, 79.2, 76.8, 72.5, 71.6, 70.8, 70.7, 68.7, 68.6, 67.3, 63.1, 57.1, 56.3, 56.1, 52.5, 47.3, 40.5, 37.8, 34.5, 24.0, 22.9, 22.4, 20.2, 18.5, and 14.8 parts per million downfield from tetramethylsilane |
| High pressure liquid chromato-graphy | Column: $\mu$Bondapak C-18 silica gel (Waters Associates, Milford, Massachusetts), 3.9 mm (i.d.) × 30 cm. Mobile phase: Methanol:aceto-nitrile: 0.05 M ammonium acetate buffer (pH 6.5) (18:46:36) Flow rate: 1.5 ml/min Detection: UV absorption at 254 nm Retention time: 4.4 min |
| Thin layer chroma-tography | Stationary phase: Silica gel 60 F-254 (Merek & Co., Rahway, N.J.) Mobile phase: Chloroform: methanol (92:8) $R_f$: 0.38 |

Biological Activity of CL-1577-B4 Compound

The antimicrobial activity of the compound of this invention against five species of gram-negative bacteria, seven species of gram-positive bacteria, four species of yeasts, and two species of fungi was determined using the microtiter dilution technique. This method is described by T. B. Conrath, "Handbook of Microtiter Procedures," Dynatech Corp., Cambridge, Mass., USA (1972); and T. L. Gavan and A. L. Barry, "Microdilution Test Procedures" in *Manual of Clinical Biology*, E. H. Lennett, Ed., American Soc. for Microbiol., Washington, D.C. USA (1980).

Each agent is suspended in a nonaqueous solvent for several minutes to sterilize the compound, or if the compound is completely soluble is water, the aqueous solution is sterilized by passage through a 0.2–0.45 $\mu$m membrane filter.

Each well of a 96-well microdilution tray is filled under aseptic conditions with 0.1 ml of Mueller-Hinton broth for antibacterial tests, or yeast extract-peptone-dextrose or buffered supplemented yeast nitrogen base for tests using fungi or yeasts.

A 0.5 ml sample of the test compound solution is added to each of the eight wells in the first row of the test plate. A microdilutor apparatus is used to simultaneously mix the contents of these wells and to transfer aliquots to each succeeding row of wells to obtain a range of serially diluted solutions; e.g., concentrations of 1000, 333, 111, 37, 12.3, 4.1, 1.37, and 0.46 $\mu$g/ml.

The last row of wells is untreated with test compound and serves as control.

Each well containing broth and test compound is inoculated with about 10 microliters of inoculum of the test microroganism. One well in the last row of wells (which is free of test compound) is not inoculated to provide a sterility control. The trays are then sealed and incubated. Media inoculated with bacteria are incubated at 37° C. for 16–24 hours, while those containing yeasts or fungi are incubated at 28° C. for 36–48 hours. During the incubation, the inoculated medium is shaken at 100–140 rpm to increase contact between the cells and the test compounds.

After the incubation period, each plate is placed on a test reading mirror and the incubation end points are observed and recorded. The lowest concentration of test compound producing inhibition of the growth of the microorganism (designated the MIC value) is used as a measure of the activity of the compound against that particular microorganism.

The data for the activity of CL-1577-B4 compound of the present invention against a variety of bacteria, yeasts, and fungi appear in Table 8. Normally, MIC values of <0.5 $\mu$g/ml up to 333 $\mu$g/ml are considered as indicative of activity; MIC values between 333 $\mu$g/ml to 1000 $\mu$g/ml are considered as indicative of marginal activity; and MIC values >1000 $\mu$g/ml are considered indicative of lack of activity. However, it was found that the potency of the compound of the present invention was of such a magnitude that the normal serial dilution concentrations described above had to be divided again by a factor of 1000; hence the MIC values presented in Table 8 are given in units of ng/ml.

TABLE 8

Antimicrobial Activity of CL-1577-B4 Compound

| Microorganism | Minimal Inhibitory Concentration (MIC) (ng/ml) |
|---|---|
| *Escherichia coli* | 4.1 |
| *Salmonella typhimurium* | <0.46 |
| *Corynebacterium sp.* | 1.4 |
| *Branhamella catarrhalis* | <0.46 |
| *Pseudomonas aeroginosa* | 333 |
| *Micrococcus luteus* | <0.46 |
| *Staphylococcus aureus* | <0.46 |
| *Streptococcus pyrogenes* | 12.3 |
| *Streptococcus phenumoniae* | <0.46 |
| *Streptococcus faecalis* | 37 |
| *Bacillus cereus* | 1.4 |
| *Bacillus megaterium* | 111 |
| *Saccharomyces cerevisiae* | 1000 |
| *Schizosaccharomyces pombe* | 4.1 |
| *Rhodotorula aurantiaca* | 12.3 |
| *Torulopsis albida* | >1000 |
| *Mucor paraciticus* | 1000 |
| *Rhizopus japonicus* | >1000 |

The in vitro cytotoxic antitumor activity of the compound of this invention against the L1210 murine leukemia cell line was determined by the method detailed in R. I. Geran, et al, "Protocols for Screening Chemical Agents and Natural Products Against Animal Tumors and Other Biological Systems," 3rd Ed., *Cancer Chemotherapy Reports*, Part 3, Vol. 3, 1–87 (1972) which is incorporated herein by reference.

From duplicate test, the compound of this invention was found to possess an IC$_{50}$ value of 0.117 ng/ml.

The in vivo antitumor activity of CL-1577-B4 compound against transplanted P388 murine leukemia in laboratory mice was determined by the method detailed in Geran, et al. cited above. The above were infected intraperitoneally on Day 0 and then administered appropriate doses of CL-1577-B4 compound on Days 1-9. The median survival time for treated mice, divided by the median survival time for infected but untreated mice is expressed as a percentage in Table 9.

TABLE 6

In Vivo Antitumor Activity of CL-1577-B4 Compound Against Transplanted P388 Murine Leukemia in Mice

| Dosage (μg/kg injection) | % T/C* |
|---|---|
| 12.50 | Toxic |
| 6.25 | Toxic |
| 3.13 | 172 |
| 1.56 | 155 |

*T/C = $\frac{\text{Median Survival Time of Treated Mice}}{\text{Medial Survival Time of Untreated Mice}} \times 100$ Preparation of Pharmaceutical Compositions For preparing pharmaceutical compositions of the compound described in this invention, inert, pharmaceutically acceptable carriers can be either solid or liquid.

Solid form preparations may include powders, tablets, dispersible granules, capsules, cachets, and suppositories. A solid carrier can be one or more substances which may also act as diluents, flavoring agents, solubilizers, lubricants, suspending agents, binders, tablet disintegrating agents; it can also be an encapsulating material.

In powders, the carrier is a finely divided solid which is in admixture with the finely divided active ingredient. In a tablet, the active ingredient is mixed with a carrier having suitable binding properties and compacted in the shape and size desired. The powders and tablets preferably contain the active ingredient in amounts ranging from about 0.001 weight percent to about one weight percent. Suitable solid carriers for powders and tablets include magnesium carbonate, magnesium stearate, talc, sugar, lactose, pectin, dextrin, starch, gelatin, tragacanth, methyl cellulose, low melting waxes, cocoa butter, and the like.

The term "preparation" is intended to include the formulation of the active compound with encapsulating material as carrier providing a capsule in which the active ingredient (with or without additional carriers) is surrounded by the encapsulating carrier, which is thus associated with it. Similarly, cachets are included. Tablets, powders, cachets, and capsules can be used as solid dosage forms suitable for oral administration.

Liquid form preparations may include solutions, suspensions, and emulsions. As an example may be mentioned water or water-propylene glycol solutions for parenteral injection. Liquid preparations can also be formulated in solution in aqueous polyethylene glycol solution. Aqueous solutions suitable for oral administration can be prepared by dissolving the active component in water followed by the addition of appropriate colorants, flavors, stabilizing, and thickening agents as desired.

Aqueous suspensions suitable for oral administration can be made by dispersing the finely divided active component in water with viscous materials such as natural or synthetic gums, resins, methyl cellulose, sodium carboxymethyl cellulose, and other well known suspending agents.

Preferably the pharmaceutical preparation is in unit dosage form. In such form, the preparation is subdivided into unit doses containing appropriate quantities of the active component. The unit dosage form can be a packaged preparation with the package containing discrete quantities of the preparation as, for example, packeted tablets, capsules, and powders, vials, or ampoules containing powders or prepared solutions.

The unit dosage form can also be a capsule, cachet, or tablet itself, or it can be the appropriate number of these in packaged form.

The quantity of active compound in a unit dose of preparation may be varied or adjusted from 0.01 mg to 10 mg according to the particular application and the potency of the active component.

In therapeutic agents for treating microbial infections, the compositions utilized in the pharmaceutical method of this invention are administered at the initial dosage of about 0.001 mg to about 0.01 mg per kilogram daily. The dosages, however, may be varied according to the requirements of the patient, and the severity of the condition being treated. Determination of the proper dose for a particular situation is within the scope of the art. Generally, treatment is initiated with smaller doses which are less than the optimum dose of the compound and thereafter the dosage is increased by small increments until the optimum effect under the circumstances is reached. For convenience, the total daily dose may be divided and administered in portions during the day if desired.

We claim:

1. A process for preparing compound CL-1577-B4, said compound having the characteristics:
    a pale yellow solid having an elemental analysis corresponding to 47.8% C; 5.74% H; 3.88% N; 30.66% O (by difference); and 11.92% S;
    an ultraviolet spectrum showing absorption At 315 nm (inflection), 271 nm (a=10.8), and 213 nm (inflection);
    an infrared spectrum showing principal absorption peaks at 3700, 3500, 3180, 2975, 2930, 1735, 1682, 1670, 1603, 1508, 1500, 1383, 1369, 1302, 1154, 1100, 1075, 1020, 990, and 859 reciprocal centimeters;
    a 200 MHz proton magnetic resonance spectrum in deuterochloroform showing principal signals at 1.10 (goublet), 1.34 (doublet), 1.39 (doublet), 1.51 (broad double doublet), 2.10 (singlet), 2.13 (doublet of doublets), 2.30 (multiplet), 2.49 (singlet), 2.50 (doublet of doublets), 2.76 (multiplet), 3.39 (doublet of doublets), 3.38–3.4 (multiplet), 3.99 (doublet of doublets), 4.11 (doublet of doublets), 4.29 (singlet), 4.63 (doublet), 4.96 (doublet of doublets), 5.68 (broad doublet), 5.79 (doublet of doublets), 5.88 (doublet), 6.17 (multiplet), 6.22 (doublet), and 6.56 (doublet of doublets) parts per million downfield from tetramethylsilane;
    and a 90.56 MHz $^{13}$C magnetic resonance spectrum in deuterochloroform showing principal signals at 193.8, 156.0, 149.8, 136.0, 132.7, 130.3, 126.3, 123.6, 100.8, 99.9, 98.4, 89.5, 84.1, 83.8, 79.5, 79.2, 76.8, 72.5, 71.6, 70.8, 70.7, 68.7, 68.6, 67.3, 63.1, 57.1, 56.3, 56.1, 52.5, 47.3, 40.5, 37.8, 34.5, 24.0, 22.9, 22.4, 20.2, 18.5, and 14.8 parts per million downfield from tetramethylsilane;
    said process comprising the steps of culturing a purified straint of actinomycete identified as ATCC 39363 under aerobic conditions in a medium comprising assimilable sources of carbon, nitrogen, and sulfur until a sufficient quantity of CL-1577A or CL-1577B intermediate compound is produced;

isolating said CL-1577A or CL-1577B compounds from said medium; and contacting said CL-1577A or CL-1577B compound with 0.1 molar methanolic HCl at a temperature of about 37° C. for a period of about thirty minutes to produce said CL-1577-$B_4$ compound and thereafter adjusting the pH of the solution to a value of about pH 5.5 and isolating said CL-1577-$B_4$ compound by conventional means.

* * * * *